United States Patent
Flohr et al.

(10) Patent No.: US 6,749,593 B1
(45) Date of Patent: Jun. 15, 2004

(54) DISPOSABLE ABSORBENT ARTICLE COMPRISING FECAL MANAGEMENT MEMBER HAVING FIBERS ORIENTED IN THE Z-DIRECTION

(75) Inventors: Andreas Flohr, Mulheim/Ruhr (DE); Georg Pescher, Bad Soden (DE); Jorg Muller, Karben (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/762,086

(22) PCT Filed: Aug. 3, 1999

(86) PCT No.: PCT/US99/17814

§ 371 (c)(1),
(2), (4) Date: Feb. 16, 2001

(87) PCT Pub. No.: WO00/07535

PCT Pub. Date: Feb. 17, 2000

(30) Foreign Application Priority Data

Aug. 7, 1998 (EP) .............................. 98114858

(51) Int. Cl.$^7$ ................................................ A61F 13/15
(52) U.S. Cl. .................................................. 604/385.01
(58) Field of Search ................................ 604/378, 383, 604/385.01

(56) References Cited

U.S. PATENT DOCUMENTS

| | | | |
|---|---|---|---|
| 2,418,907 A | | 4/1947 | Schreiber |
| 3,604,422 A | * | 9/1971 | Sabee |
| 3,655,921 A | | 4/1972 | Busick et al. |
| 3,903,768 A | | 9/1975 | Amberg et al. |
| 3,967,623 A | | 7/1976 | Butterworth et al. |
| 4,047,531 A | | 9/1977 | Karami |
| 4,077,410 A | * | 3/1978 | Butterworth et al. |
| 4,324,246 A | * | 4/1982 | Mullane et al. |
| 4,681,577 A | | 7/1987 | Stern et al. |
| 4,723,954 A | * | 2/1988 | Pieniak |
| 4,758,241 A | | 7/1988 | Papajohn |
| 5,037,409 A | | 8/1991 | Chen et al. |
| 5,037,416 A | | 8/1991 | Allen et al. |
| 5,062,840 A | | 11/1991 | Holt et al. |
| 5,124,197 A | | 6/1992 | Bernardin et al. |
| 5,134,007 A | | 7/1992 | Reising et al. |
| 5,147,343 A | | 9/1992 | Kellenberger |
| 5,149,335 A | | 9/1992 | Kellenberger et al. |
| 5,171,236 A | | 12/1992 | Dreier et al. |
| 5,236,430 A | | 8/1993 | Bridges |
| 5,254,194 A | | 10/1993 | Ott et al. |
| 5,306,384 A | | 4/1994 | Stutt |
| 5,364,382 A | | 11/1994 | Latimer et al. |

(List continued on next page.)

FOREIGN PATENT DOCUMENTS

| | | |
|---|---|---|
| DE | 93 07 894 U1 | 9/1993 |
| DE | 93 07 894.3 | 9/1993 |
| EP | 0 139 484 A1 | 5/1985 |
| EP | 0 139 484 B1 | 11/1989 |
| EP | 0 820 746 A1 | 1/1998 |
| EP | 0 355 740 B2 | 8/1999 |
| FR | 2504799 | 11/1982 |
| GB | 2 171 016 A | 8/1986 |
| GB | 2 294 397 A | 5/1996 |
| GB | 2 294 901 A | 5/1996 |
| WO | WO 90/14061 A1 | 11/1990 |
| WO | WO 91/01766 A1 | 2/1991 |

(List continued on next page.)

*Primary Examiner*—Dennis Ruhl
(74) *Attorney, Agent, or Firm*—Jack L. Oney, Jr.; Ken K. Patel

(57) ABSTRACT

The present invention relates to a disposable absorbent article having a fecal management member intended to handle fluids including in particular high viscosity fluids such as feces and menses. The fecal management member includes a plurality of fibers oriented in the z-direction which lead to improved fluid transportation in the z-direction and is positioned intermediate the topsheet and the backsheet of the disposable absorbent article.

10 Claims, 3 Drawing Sheets

U.S. PATENT DOCUMENTS

| | | |
|---|---|---|
| H1511 H | 12/1995 | Chappell et al. |
| 5,476,459 A | 12/1995 | Yang |
| 5,575,187 A | 11/1996 | Dieterlen |
| 5,611,791 A | 3/1997 | Gorman et al. |
| 5,628,741 A | 5/1997 | Buell et al. |
| 5,645,672 A | 7/1997 | Dobrin |
| 5,672,164 A | 9/1997 | Crane |
| 5,681,302 A | 10/1997 | Melbye et al. |
| 5,683,374 A | 11/1997 | Yamamoto et al. |
| 5,782,156 A | 7/1998 | Collins |
| 6,026,725 A | 2/2000 | Okonski |
| 6,043,836 A | 3/2000 | Kerr et al. |
| 6,183,458 B1 | 2/2001 | Ahlstrand et al. |
| 6,222,092 B1 | 4/2001 | Hansen et al. |
| 6,350,223 B1 | 2/2002 | Niedermeyer |
| 6,375,644 B2 | 4/2002 | Mizutani |
| 6,413,338 B1 | 7/2002 | DiPalma |
| 6,417,426 B1 | 7/2002 | Takai et al. |
| 6,436,081 B1 | 8/2002 | Wada et al. |

FOREIGN PATENT DOCUMENTS

| | | |
|---|---|---|
| WO | WO 93/01780 A1 | 2/1993 |
| WO | WO 93/22997 A1 | 11/1993 |
| WO | WO 94/05243 A2 | 3/1994 |
| WO | WO 94/05244 A1 | 3/1994 |
| WO | WO 96/06588 A1 | 3/1996 |
| WO | WO 97/00656 A1 | 1/1997 |
| WO | WO 97/18783 A1 | 5/1997 |
| WO | WO 97/18784 A1 | 5/1997 |
| WO | WO 98/25560 A1 | 6/1998 |
| WO | WO 98/42289 A1 | 10/1998 |
| WO | WO 00/06067 A2 | 2/2000 |
| WO | WO 00/06069 A1 | 2/2000 |
| WO | WO 00/06073 A1 | 2/2000 |

* cited by examiner

DISPOSABLE ABSORBENT ARTICLE COMPRISING FECAL MANAGEMENT MEMBER HAVING FIBERS ORIENTED IN THE Z-DIRECTION

FIELD OF THE INVENTION

The present invention relates to articles which absorb and/or contain bodily exudates, including disposable absorbent articles such as diapers, adult incontinence products, sanitary napkins and the like. More particularly, the invention relates to disposable absorbent articles which comprise a fecal management member having a plurality of fibers oriented in the z-direction.

BACKGROUND OF THE INVENTION

Absorbent articles comprising fecal management members such as diapers, adult incontinence products, or sanitary napkins are well known in the art. Such fecal management members acquire and optionally distribute and retain fluid body exudates such as urine and in particulate highly viscous body exudates such as menses, or fecal material deposited thereon by the wearer. Examples of such fecal management member can be found in U.S. Pat. No. 5,364,382 issued to Latimer et al. on Nov. 15, 1994 and in European Patent Application EP820746 published on Jan. 27, 1998, in the name of Palumbo et al.

To date, the liquid pervious/absorbent parts of most fecal management members in the art have been manufactured using, inter alia, essentially sheet-like materials. Most of the sheet-like materials used for this purpose contain at least some fibrous base materials because of the convenience to make liquid pervious/absorbent (i.e. porous) structures from fibrous materials. Conventional manufacturing techniques for such sheet-like materials form a sheet of fibers by orienting the fibers in the x,y-direction and then stabilize the sheet by bonding the fibers to each other at some of the cross points of the fibers.

However, the x,y-orientation of the fibers has some inherent disadvantages for the handling of fluids in particular highly viscous fluids by the fecal management member.

One objective of most fecal management members is to draw fluid and in particular highly viscous fluid away from the surface of the fluid insult into the bulk of the structure, i.e. to move the fluid perpendicular to the surface of the structure. The fluid transport in the fibrous parts of the fecal management member often happens along the lengths of the fibers caused by mechanisms such as wetting the surfaces of the individual fibers. Therefore, conventional fecal management members have the disadvantage of at least partially distributing the fluid along the orientation of the comprised fibers, i.e. in the x,y-direction. Thus, the fluid remains in close proximity to the surface of the fluid insult, i.e. close to the skin of the user.

To improve on moving fluid away from the skin of the user, it has been taught to provide absorbent articles having topsheets with a fibrous layer on their body facing side (see for example U.S. Pat. No. 3,967,623 issued to Butterworth on Jul. 6, 1976, or Belgium patent publication No. 1007041 issued to Filipovic on Feb. 28, 1995). These topsheets are intended to have the desirable characteristics of a fabric like facing material.

However, in order to achieve the fabric-like touch the fibrous layer comprised on the user facing side of these topsheets must not comprise stiff fibers. Stiff fibers could poke into the skin of the wearer leading to an undesirable wearing experience.

On the other hand, stiffness of the fibers in the fibrous layer is preferred in the context of fluid handling, in particular in the handling of highly viscous fluids. To maintain the fluid handling under usage conditions (such as the wearer sitting on the absorbent article), the fecal management member must preserve its structure as much as possible. Therefore, it must comprise fibers of a certain stiffness and resiliency.

Hence, it is an object of the present invention to provide a disposable absorbent article having a fecal management member which has an improved fluid transport in the z-direction by orienting a plurality of fibers in the z-direction. The fecal management member is covered with a topsheet to address the deficiencies stated above to avoid fiber contact with the skin of the user.

It is a further object of the present invention, to provide such a disposable absorbent article wherein the fecal management member provides sufficient pressure resistance and/or resiliency.

SUMMARY OF THE INVENTION

The present invention relates to disposable absorbent articles comprising a topsheet, a backsheet, and a fecal management member positioned intermediate the topsheet and the backsheet. The fecal management member comprises a first component which includes a support element. This first component has an inner major surface and an outer major surface. In addition, the fecal management member comprises a second component including a plurality of fibers. The second component has a thickness dimension perpendicular to the major surfaces of the first component and the fibers have a length dimension. The fibers of the second component of the fecal management member are attached to the support element. In an uncompressed state of the fecal management member, the fibers are oriented substantially perpendicular to the inner major surface of the first component of the fecal management member (i.e. substantially parallel to the thickness dimension of the second component) and the fibers have a length which is substantially equivalent to the thickness dimension of the second component of the fecal management member. In the disposable absorbent article, the fecal management member is oriented such that the second component is positioned intermediate the topsheet and the second component. In the disposable absorbent article of the present invention less than 50% of the fibers comprised in the second component of the fecal management member are joined to the topsheet.

BRIEF DESCRIPTION OF THE DRAWINGS

While the specification concludes with claims particularly pointing out and distinctly claiming the subject matter which is regarded as the present invention, it is believed that the description will be better understood from the following descriptions which are taken in conjunction with the accompanying drawings in which like designations are used to designate substantially identical elements.

DETAILED DESCRIPTION OF THE INVENTION

Figure 1:
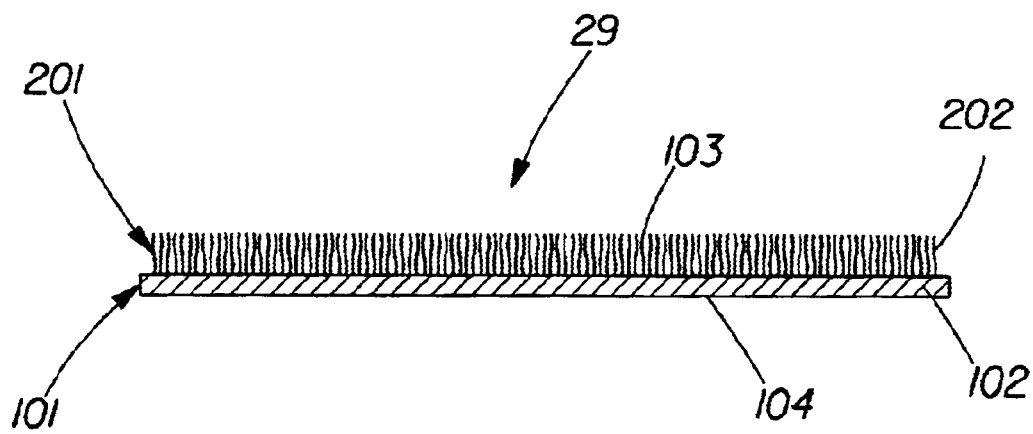
FIG. 1 is a side view of a fecal management member suitable for the present invention.

FIG. 1 shows a fecal management member 29 suitable for the present invention including a first component 101 comprising a support element 102 and a second component 201 comprising a plurality of fibers 202. The support element 102 has a inner major surface 103 and an outer major surface 104.

As used herein, the term "fecal management member" refers to devices which are intended to handle fluids in particular aqueous fluids such as body exudates, including in particular highly viscous body exudates such as feces and menses. The term "handling fluids" as used herein refers to capabilities such as to acquire fluids, to distribute fluids, to store liquids, to retain fluids, or the like. As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner).

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "uncompressed state" as used herein refers to a state of a fecal management member suitable for the present invention in which none of the surfaces of the fecal management member is exposed to an external compressive load. In addition, a fecal management member in an uncompressed state has not been exposed to compressive loads to an extent sufficient to alter its original configuration, in particular to alter the orientation of the fibers of the second component.

The term "substantially perpendicular" as used herein refers to a configuration in which the angle between the fiber and the surface is more than 60 degrees, preferably more than 70 degrees, more preferably 80 degrees, most preferably 90 degrees.

The term "z-direction" as used herein refers to the direction substantially perpendicular to the inner major surface of the support element comprised in the first component of a fecal management member suitable for the present invention.

A suitable support element 102 may be manufactured from a wide range of materials such as woven and nonwoven materials (e.g., a nonwoven web of fibers); polymeric materials such as apertured formed thermoplastic films, apertured plastic films, and thermoplastic films including hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. When the support element comprises a nonwoven web, the web may be manufactured by a wide number of known techniques. For example, the web may be spunbonded, carded, wet-laid, melt-blown, hydroentangled, resin-bonded, combinations of the above, or the like. The support element may also be a plurality of fibers, a porous film, a breathable material, an apertured nonwoven web, strips of nonwoven material, a sheet of loop material, strips of thermoplastic film, a hotmelt material, or strips of hotmelt material.

The basis weight of the support element 102 of the first component is between 6 and 1000 grams per square meter, preferably between 8 and 500 grams per square meter, even more preferably between 10 and 100 grams per square meter, most preferably between 12 and 55 grams per square meter.

In a fecal management member suitable for the present invention, the fibers 202 of the second component 201 are joined to the inner major surface 103 of the support element 102. Preferably, the fibers are joined to the surface by a means selected from the group of: adhesive bonding, thermo-bonding.

Many different types of fibers 202 are suitable for use in the second component 201 of the present invention. Suitable fibers include natural fibers (modified or unmodified), as well as synthetically made fibers. Examples of suitable unmodified/modified natural fibers include cotton, Esparto grass, bagasse, hemp, flax, silk, wool, wood pulp, chemically modified wood pulp, jute, rayon, ethyl cellulose, and cellulose acetate. Suitable synthetic fibers can be made from polyolefins such as polyethylene (e.g. PULPEX™) or polypropylene, polyamides such as nylon, polyester such as DACRON™ or KODEL™, polyethyleneterepthalate, polyvinyl chloride, polyvinyl fluoride, polytetrafluoroethylene, polyvinylidene chloride, polyacrylics such as ORLON™, polyvinyl acetate, polyethylvinyl acetate, non-soluble or soluble polyvinyl alcohol, polyurethanes, polystyrenes, and the like. The fibers included in the second component may comprise solely natural fibers, solely synthetic fibers, or any compatible combination of natural and synthetic fibers.

Preferably, the fibers used in the manufacture of the second component are selected from the group of: polyester, polyamide, polyethylene, polypropylene, polyethyleneterepthalate. These fibers have been used widely in fecal management members because of their favorable combination of raw material properties such as resiliency and durability, their ease of conversion, and their cost, and the like.

The basis weight of the fibers of the second component is between 6 and 1000 grams per square meter, preferably between 8 and 500 grams per square meter, even more preferably between 10 and 100 grams per square meter, most preferably between 12 and 55 grams per square meter.

An increased size of the fibers of the second component leads to improved pressure resistance and resiliency of the second component, whereas reduced fiber size leads to smaller capillaries and potentially improved fluid handling. Preferably, the fibers of the second component have a size between 1 denier and 18 denier, more preferably between 3 denier and 15 denier, most preferably between 5 denier and 12 denier.

The cut length of the fibers of the second component determines the thickness dimension of the second component. Preferably, the cut length is more than 0.1 millimeters and less than 25 millimeters, more preferably more than 0.2 millimeters and less than 10 millimeters, most preferably more than 0.5 millimeters and less than 5 millimeters.

In some preferable embodiments of the present invention, the fecal management member comprises a first region and a second region wherein the thickness of the second component in the first region is larger than the thickness of the second component in the second region.

For fecal management members, a hydrophilicity gradient in the z-direction such that the more hydrophobic parts being oriented towards the expected liquid insults may be advantageous. The increasing hydrophilicity of the fecal management member in the z-direction may support that the fluid is drawn inside the fecal management member away from the surface. In addition, the more hydrophobic a layer of the fecal management member is, the less likely it is to retain fluid after the insult. Hence, a more hydrophobic user facing surface of the fecal management member may lead to an improved dry touch of the fecal management member even after repeated fluid insults.

In a preferred embodiment of a fecal management member suitable for the present invention, the fecal management member exhibits a gradient of increasing hydrophilicity from the second component to the first component in a direction substantially perpendicular to the surface of the fluid insult. The first component and/or the second component may also have hydrophilicity gradients along their thickness dimensions, the gradients having the orientation as the overall hydrophilicity gradient.

Another key property of a fecal management member suitable for the present invention is its resistance to compression under pressure. As used herein, the term "compression resistance" refers to the percentage caliper a fecal management member exhibits under a certain load compared to its caliper in the unloaded condition. In use, the fecal management member must be able, at least partially, to maintain its openness under the load of the user to be able to readily accept fluids. Preferably, the fecal management member has a compression resistance of at least 30% under an applied pressure of 981 Newton per square centimeter, more preferably the fecal management member has a compression resistance of at least 40% under an applied pressure of 981 Newton per square centimeter, most preferably the fecal management member has a compression resistance of at least 50% under an applied pressure of 981 Newton per square centimeter.

Another key component is the resiliency of the fecal management member 29. As used herein, the term "resiliency" refers to the percentage of recovered caliper after a fecal management member has been compressed under a certain load for a certain time. In order to remain open, the fecal management member must have a sufficient resiliency to withstand the forces of packaging and those applied by the user. Preferably, the fecal management member has a resiliency of at least 50% after 30 seconds under an applied pressure of 981 Newton per square centimeter, more preferably, the fecal management member has a resiliency of at least 75% after 30 seconds under an applied pressure of 981 Newton per square centimeter, most preferably, the fecal management member has a resiliency of at least 85% after 30 seconds under an applied pressure of 981 Newton per square centimeter.

In the disposable absorbent article of the present invention, the fecal management member 29 is oriented such that the second component 201 is adjacent the topsheet 24, i.e. the second component 201 is positioned intermediate the topsheet 24 and the first component 101.

In the disposable absorbent article according to the present invention, less than 50% of the fibers 202 are joined to the topsheet, preferably less than 25%, more preferably less than 10%, most preferably none of the fibers are joined to the topsheet 24.

The support element 102 in the disposable absorbent article of the present invention may be or may not be joined to the backsheet or the absorbent core of the disposable absorbent article.

Figure 2:
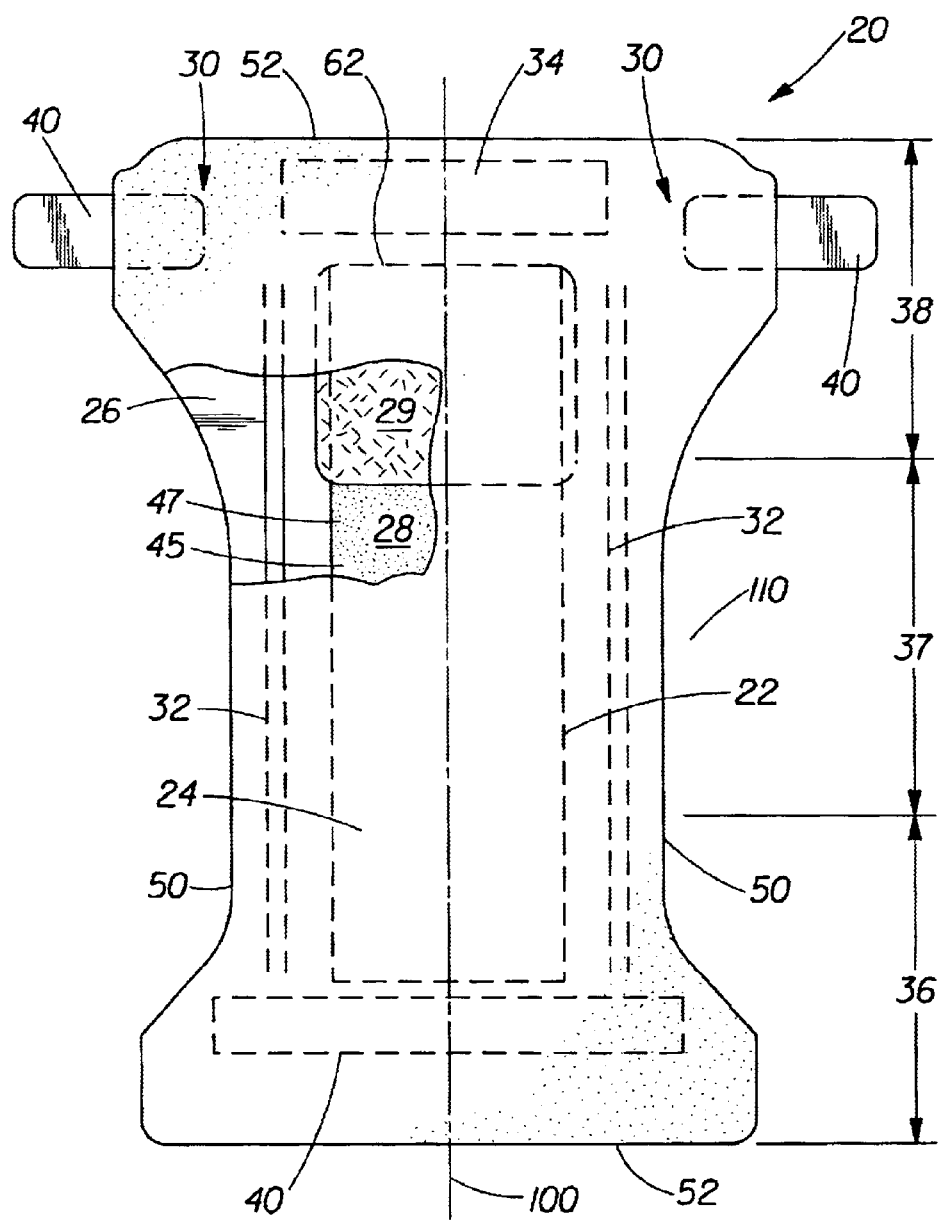
FIG. 2 is a plan view of an absorbent article embodiment of the present invention having portions cut away to reveal the underlying structure, the garment-facing surface of the diaper facing the viewer.

A preferred embodiment of an absorbent article of the present invention is the unitary disposable absorbent article, diaper 20, shown in FIG. 2. As used herein, the term "diaper" refers to an absorbent article generally worn by infants and incontinent persons about the lower torso. The present invention is also applicable to other absorbent articles such as incontinence briefs, incontinence undergarments, absorbent inserts, diaper holders and liners, feminine hygiene garments, and the like.

A "unitary" absorbent article refers to absorbent articles which are formed of separate parts united together to form a coordinated entity so that they do not require separate manipulative parts like a separate holder and liner.

FIG. 2 is a plan view of the diaper 20 of the present invention in a flat-out, state with portions of the structure being cut-away to more clearly show the construction of the diaper 20. The portion of the diaper 20 which faces the wearer is oriented towards the viewer. As shown in FIG. 2, the diaper 20 preferably comprises a liquid pervious topsheet 24; a liquid impervious backsheet 26; an absorbent core 28, which is preferably positioned between at least a portion of the topsheet 24 and the backsheet 26; a fecal management member 29 positioned between the topsheet 24 and the absorbent core 28; side panels 30; elasticized leg cuffs 32; an elastic waist feature 34; and a fastening system generally designated 40. Diaper 20 is shown in FIG. 2 to have a front waist region 36, a rear waist region 38 opposed to the front waist region 36 and a crotch region 37 located between the front waist region and the rear waist region. The periphery of the diaper 20 is defined by the outer edges of the diaper 20 in which the longitudinal edges 50 run generally parallel to the longitudinal centerline 100 of the diaper 20 and the end edges 52 run between the longitudinal edges 50 generally parallel to the lateral centerline 110 of the diaper 20.

The chassis 22 of the diaper 20 comprises the main body of the diaper 20. The chassis 22 comprises at least a portion of the absorbent core 28 and preferably an outer covering layer including the topsheet 24 and the backsheet 26. If the absorbent article comprises a separate holder and a liner, the chassis 22 generally comprises the holder and the liner. (For example, the holder may comprise one or more layers of material to form the outer cover of the article and the liner may comprise an absorbent assembly including a topsheet, a backsheet, and an absorbent core. In such cases, the holder and/or the liner may include a fastening element which is used to hold the liner in place throughout the time of use.) For unitary absorbent articles, the chassis 22 comprises the main structure of the diaper with other features added to form the composite diaper structure. While the topsheet 24, the backsheet 26, and the chassis 22 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 issued to Buell on Sep. 9, 1992; and U.S. Pat. No. 5,221,274 issued to Buell on Jun. 22, 1993. Other suitable diaper chassis design are disclosed in U.S. Pat. No. 5,569,232 entitled "Absorbent Article With Multiple Zone Structural Elastic-Like Film Web Extensible Waist Feature" which issued to Roe et al. on Sep. 10, 1996; U.S. Pat. No. 5,554,144 entitled "Absorbent Article With Multiple Zone Structural Elastic-Like Film Web Extensible Waist Feature" which issued to Roe et al. on Sep. 10, 1996; U.S. Pat. No. 5,554,143 entitled "Absorbent Article With Multiple Zone Structural Elastic-Like Film Web Extensible Waist Feature" which issued to Roe et al. on Sep. 10, 1996; U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,556,394 entitled "Absorbent Article With Multiple Zone Structural Elastic-Like Film Web Extensible Waist Feature" which issued to Roe et al. on Sep. 17, 1996. Each of these references is hereby incorporated by reference herein.

The backsheet 26 is generally that portion of the diaper 20 positioned adjacent the garment facing surface 45 of the absorbent core 28 which prevents the exudates absorbed and contained therein from soiling articles which may contact the diaper 20, such as bedsheets and undergarments. In preferred embodiments, the backsheet 26 is impervious to liquids (e.g., urine) and comprises a thin plastic film such as a thermoplastic film having a thickness of about 0.012 mm (0.5 mil) to about 0.051 mm (2.0 mils). Suitable backsheet films include those manufactured by Tredegar Industries Inc. of Terre Haute, Ind. and sold under the trade names X15306, X10962 and X10964. Other suitable backsheet materials may include breathable materials which permit vapors to escape from the diaper 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont and copending U.S. patent application Ser. No. 081744,487, filed on Nov. 6, 1996 in the name of Curro. Other breathable backsheets including nonwoven webs and apertured formed films are described in U.S. Pat. No. 5,571,096 issued to Dobrin et al. on Nov. 5, 1996. Each of these references is hereby incorporated by reference herein.

The backsheet 26, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials. The SELF web includes a strainable network having at least two contiguous, distinct, and dissimilar regions. Preferably, one of the regions is configured so that it will exhibit resistive forces in response to an applied axial elongation in a direction parallel to the predetermined axis before a substantial portion of the other region develops significant resistive forces to the applied elongation. At least one of the regions has a surface-pathlength which is greater than that of the other region as measured substantially parallel to the predetermined axis while the material is in an untensioned condition. The region exhibiting the longer surface-pathlength includes one or more deformations which extend beyond the plane of the other region. The SELF web exhibits at least two significantly different stages of controlled resistive force to elongation along at least one predetermined axis when subjected to an applied elongation in a direction parallel to the predetermined axis. The SELF web exhibits first resistive forces to the applied elongation until the elongation of the web is sufficient to cause a substantial portion of the region having the longer surface-pathlength to enter the plane of applied elongation, whereupon the SELF web exhibits second resistive forces to further elongation. The total resistive forces to elongation are higher than the first resistive forces to elongation provided by the first region. SELF webs suitable for the present invention are more completely described in U.S. Pat. No. 5,518,801 entitled Web Materials Exhibiting Elastic-Like Behavior, which issued to Chappell, et, al. on May 21, 1996, which is incorporated herein by reference. In alternate embodiments, the backsheet 26 may comprise elastomeric films, foams, strands, or combinations of these or other suitable materials with nonwovens or synthetic films.

The backsheet 26 may be joined to the topsheet 24, the absorbent core 28 or any other element of the diaper 20 by any attachment means known in the art. For example, the attachment means may include a uniform continuous layer of adhesive, a patterned layer of adhesive, or an array of separate lines, spirals, or spots of adhesive. One preferred attachment means comprises an open pattern network of filaments of adhesive as disclosed in U.S. Pat. 4,573,986 entitled "Disposable Waste-Containment Garment", which issued to Minetola et al. on Mar. 4, 1986. Other suitable attachment means include several lines of adhesive filaments which are swirled into a spiral pattern, as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Each of these patents are incorporated herein by reference. Adhesives which have been found to be satisfactory are manufactured by H.B. Fuller Company of St. Paul, Minn. and marketed as HL-1258. Alternatively, the attachment means may comprise heat bonds, pressure bonds, ultrasonic bonds, dynamic mechanical bonds, or any other suitable attachment means or combinations of these attachment means as are known in the art.

The topsheet 24 is preferably positioned adjacent the body surface 47 of the absorbent core 28 and may be joined thereto and/or to the backsheet 26 by any attachment means known in the art. Suitable attachment means are described above with respect to means for joining the backsheet 26 to other elements of the diaper 20. In one preferred embodiment of the present invention, the topsheet 24 and the backsheet 26 are joined directly to each other in some locations and are indirectly joined together in other locations by directly joining them to other elements of the diaper 20.

The topsheet 24 is preferably compliant, soft feeling, and non-irritating to the wearer's skin. Further, at least a portion of the topsheet 24 is liquid pervious, permitting liquids to readily penetrate through its thickness. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the absorbent assemblies include fibers, the fibers may be spunbond, carded, wet-laid, meltblown, hydroentangled, or otherwise processed as is known in the art. One suitable topsheet 24 comprising a web of staple length polypropylene fibers is manufactured by Veratec, Inc., a Division of International Paper Company, of Walpole, Mass. under the designation P-8.

Suitable formed film topsheets are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. Other suitable topsheets 30 are made in accordance with U.S. Pat. Nos. 4,609,518 and 4,629,643 which issued to Curro et al. on Sep. 2, 1986 and Dec. 16, 1986, respectively, and both of which are incorporated herein by reference. Such formed films are available from The Procter & Gamble Company of Cincinnati, Ohio as "DRI-WEAVE" and from Tredegar Corporation of Terre Haute, Ind. as "CLIFF-T."

Preferably, the topsheet 24 is made of a hydrophobic material or is treated to be hydrophobic in order to isolate the wearers skin from liquids contained in the absorbent core 28. If the topsheet 24 is made of a hydrophobic material, preferably at least the upper surface of the topsheet 24 is treated to be hydrophilic so that liquids will transfer through the topsheet more rapidly. This diminishes the likelihood that body exudates will flow off the topsheet 24 rather than being drawn through the topsheet 24 and being absorbed by the absorbent core 28. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating surfactant in the topsheet can be found in U.S. Statutory Invention Registration No. H1670, published on Jul. 1, 1997 in the names of Aziz et al. Each of these references is hereby incorporated by reference herein.

Any portion of the topsheet 24 may be coated with a lotion as is known in the art. Examples of suitable lotions include those described in U.S. Pat. No. 5,607,760 entitled "Disposable Absorbent Article Having A Lotioned Topsheet Containing an Emollient and a Polyol Polyester Immobilizing Agent" which issued to Roe on Mar. 4, 1997; U.S. Pat. No. 5,609,587 entitled "Diaper Having A Lotioned Topsheet Comprising A Liquid Polyol Polyester Emollient And An Immobilizing Agent" which issued to Roe on Mar. 11, 1997; U.S. Pat. No. 5,635,191 entitled "Diaper Having A Lotioned Topsheet Containing A Polysilozane Emollient" which issued to Roe et al. on Jun. 3, 1997; and U.S. Pat. No. 5,643,588 entitled "Diaper Having A Lotioned Topsheet" which issued to Roe et al. on Jul. 1, 1997. The topsheet may also include or be treated with antibacterial agents, some examples of which are disclosed in PCT Publication No. WO 95/124173 entitled "Absorbent Articles Containing Antibacterial Agents in the Topsheet For Odor Control" which was published on Sep. 14, 1995 in the name of Johnson. Further, the topsheet 24, the backsheet 26 or any portion of the topsheet or backsheet may be embossed and/or matte finished to provide a more cloth like appearance.

In some embodiments, the topsheet may comprise apertures to be able to effective handle in particular high viscosity fluids such as menses, feces, or the like. Preferably, the apertures have a size of at least 0.2 $mm^2$.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). However, the total absorbent capacity of the absorbent core 28 should be compatible with the design loading and the intended use of the diaper 20.

Exemplary absorbent structures for use as the absorbent assemblies are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; and U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994.

The diaper 20 may also comprise at least one elastic waist feature 34 that helps to provide improved fit and containment. The elastic waist feature 34 is generally intended to elastically expand and contract to dynamically fit the wearer's waist. The elastic waist feature 34 preferably extends at least longitudinally outwardly from at least one waist edge 62 of the absorbent core 28 and generally forms at least a portion of the end edge 52 of the diaper 20. Disposable diapers are often constructed so as to have two elastic waist features, one positioned in the first waist region 36 and one positioned in the second waist region 38. Further, while the elastic waist feature 34 or any of its constituent elements may comprise one or more separate elements affixed to the diaper 20, the elastic waist feature 34 may be constructed as an extension of other elements of the diaper 20, such as the backsheet 26, the topsheet 24, or both the backsheet 26 and the topsheet 24.

The elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No 5, 151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989. All of the above mentioned references are incorporated herein by reference.

The diaper 20 may also include a fastening system 40. The fastening system 40 preferably maintains the first waist region 36 and the second waist region 38 in an overlapping configuration so as to provide lateral tensions about the circumference of the diaper 20 to hold the diaper 20 on the wearer. The fastening system 40 preferably comprises tape tabs and/or hook and loop fastening components, although any other known fastening means are generally acceptable. Some exemplary fastening systems are disclosed in U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; and the herein before referenced U.S. Pat. No. 5,151,092 issued to Buell on Sep. 9, 1992; and U.S. Pat. No. 5,221,274 issued to Buell on Jun. 22, 1993. The fastening system may also provide a means for holding the article in a disposal configuration as disclosed in U.S. Pat. No. 4,963,140 issued to Robertson et al. on Oct. 16, 1990. Each of these patents is incorporated herein by reference.

The diaper 20 may also comprise side panels 30. The side panels 30 may be elastic or extensible to provide a more comfortable and contouring fit by initially conformably fitting the diaper 20 to the wearer and sustaining this fit throughout the time of wear well past when the diaper 20 has been loaded with exudates since the elasticized side panels 30 allow the sides of the diaper 20 to expand and contract. The side panels 30 may also provide more effective application of the diaper 20 because even if the diaperer pulls one elasticized side panel 30 farther than the other during application, the diaper 20 will "self-adjust" during wear.

While the diaper 20 of the present invention preferably has the side panels 30 disposed in the second waist region 38, the diaper 20 may be provided with side panels 30 disposed in the first waist region 36 or in both the first waist region 36 and the second waist region 38. The side panels 30 may be constructed in any suitable configurations. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; and U.S. Pat. No. 5,221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; U.S. patent application Ser. No. 08/155,048 entitled "Absorbent Article With Multi-Directional Extensible Side Panels" filed Nov. 19, 1993 in the names of Robles, et al.; each of which is incorporated herein by reference.

The diaper 20 preferably further includes leg cuffs 32 which provide improved containment of liquids and other body exudates. Leg cuffs may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs.

Embodiments of the absorbent article of the present invention may also include pockets for receiving and containing waste, spacers which provide voids for waste, barriers for limiting the movement of waste in the article, compartments or voids which accept and contain waste materials deposited in the diaper, and the like, or any combinations thereof. Examples of pockets and spacers for use in absorbent products are described in U.S. Pat. No. 5,514,121 issued to Roe et al. on May 7,1996, entitled "Diaper Having Expulsive Spacer"; U.S. Pat. No. 5,171,236 issued to Dreier et al on Dec. 15, 1992, entitled "Disposable Absorbent Article Having Core Spacers"; U.S. Pat. No. 5,397,318 issued to Dreier on Mar. 14, 1995, entitled "Absorbent Article Having A Pocket Cuff"; U.S. Pat. No. 5,540,671 issued to Dreier on Jul. 30, 1996, entitled "Absorbent Article Having A Pocket Cuff With An Apex"; and PCT Application WO 93/25172 published Dec. 3, 1993, entitled "Spacers For Use In Hygienic Absorbent Articles And Disposable Absorbent Articles Having Such Spacer"; and U.S. Pat. No. 5,306,266, entitled "Flexible Spacers For Use In Disposable Absorbent Articles", issued to Freeland on Apr. 26, 1994. Examples of compartments or voids are disclosed in U.S. Pat. No. 4,968,312, entitled "Disposable Fecal Compartmenting Diaper", issued to Khan on Nov. 6, 1990; U.S. Pat. No. 4,990,147, entitled "Absorbent Article With Elastic Liner For Waste Material Isolation", issued to Freeland on Feb. 5, 1991; U.S. Pat. No. 5,62,840, entitled "Disposable Diapers", issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets", issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Pat. No. WO 94/14395 entitled "Absorbent Article Having An Upstanding Transverse Partition" published Jul. 7, 1994 in the name of Freeland, et al.; and U.S. 5,653,703 Absorbent Article Having Angular Upstanding Transverse Partition, issued Aug. 5, 1997 to Roe, et al.

In addition to or in place of the voids, pockets and barriers, described above, embodiments of the present invention may include a fecal management element 120 capable of effectively and efficiently accepting, storing and/or immobilizing viscous fluid bodily waste, such as runny feces. The fecal management element 120 can be located anywhere in the article, including the crotch region or either waist region, or may be associated with or be included in any structure or element such as the core 28, a leg cuff, etc. In preferred embodiments, the fecal management element 120 is located in the region of the article that is near the user's perianal region when used. This helps ensure that any waste discharged is deposited on or near the fecal management element 120.

The diaper 20 embodiment of the present invention may be applied to a wearer by positioning one of the waist regions, preferably the rear waist region 38, under the wearer's back and drawing the remainder of the diaper 20 between the wearer's legs. The other waist region, preferably the front waist region 36, is positioned across the front of the wearer. The diaperer then wraps the side panels 30 around the wearer such that the front waist region 36 and the rear waist region 38 are in an overlapping configuration. The side panels 30 will typically be extended and tensioned during this operation so as to conform to the size and shape of the wearer. The fastening system 40 is secured to effect a side closure.

The fecal management member may be positioned at different regions within the absorbent article of the present invention. In one embodiment a fecal management member suitable for the present invention may be positioned at least in the back waist region of the absorbent article, so that it is aligned with the anus of the user where it can be most effective in managing fecal material deposited onto the fecal management member. In another embodiment of the absorbent article of the present invention, the fecal management member may extend into the front waist region, crotch region, and back waist region. In some embodiments, it may also be desirable that the fecal management member extends over the entire length of the absorbent article.

One possible way to manufacture a fecal management member suitable for the present invention is the flocking technique well known in the art.

What is claimed is:

1. A disposable absorbent article comprising a topsheet, a backsheet and a fecal management member intermediate said topsheet and said backsheet, said fecal management member comprising a first component comprising a support element and having an inner major surface and an outer major surface and a second component comprising a plurality of fibers and having a thickness dimension perpendicular to said major surfaces, said fibers having a length dimension, said fibers being joined to said inner major surface of said support element, said fibers being oriented substantially perpendicular to said inner major surface, the length of said fibers being substantially equivalent to the thickness dimension of said second component in a uncompressed state, said fecal management member being oriented such that said second component is positioned intermediate said topsheet and said first component and characterized in that less than 50% of said fibers are joined to said topsheet, said second component having a first region and a second region wherein the thickness of said first region is larger than the thickness of said second region in an uncompressed state of said fecal management member.

2. The disposable absorbent article according to claim 1 wherein said fecal management member has a resiliency of at least 85% after 30 seconds under an applied load of 981 $N/cm^2$.

3. The disposable absorbent article according to claim 1 wherein said fecal management member has a Compression Resistance of at least 30% under an applied load of 981 $N/cm^2$.

4. A disposable absorbent article according to claim 1 wherein said fibers have a basis weight between 6 and 1000 grams per square meter.

5. A disposable absorbent article according to claim 1 wherein said support element has basis weight between 6 and 1000 grams per square meter.

6. A disposable absorbent article according to claim 1 wherein the fibers of said second component are joined to said support element by a means selected from the group of adhesive bonding, thermo-bonding.

7. A disposable absorbent article according to claim 1 wherein the fibers of said second component are formed from one or more polymers selected from the group of polyester, polyamide, polyethylene, polypropylene, polyethyleneterepthalate.

8. A disposable absorbent article according to claim 1 wherein said first and said second component of said fecal management element exhibit a gradient of increasing hydrophilicity from the second component to the first component.

9. The disposable absorbent article according to claim 1 wherein said disposable absorbent article has a rear waist region and a front waist region, said fecal management member being positioned in at least said rear waist region of said disposable absorbent article.

10. A disposable absorbent article according to claim 1 wherein said topsheet comprises apertures of at least 0.2 $mm^2$.

* * * * *

UNITED STATES PATENT AND TRADEMARK OFFICE
CERTIFICATE OF CORRECTION

PATENT NO. : 6,749,593 B1  Page 1 of 1
DATED : June 15, 2004
INVENTOR(S) : Flohr et al.

Figure 3:
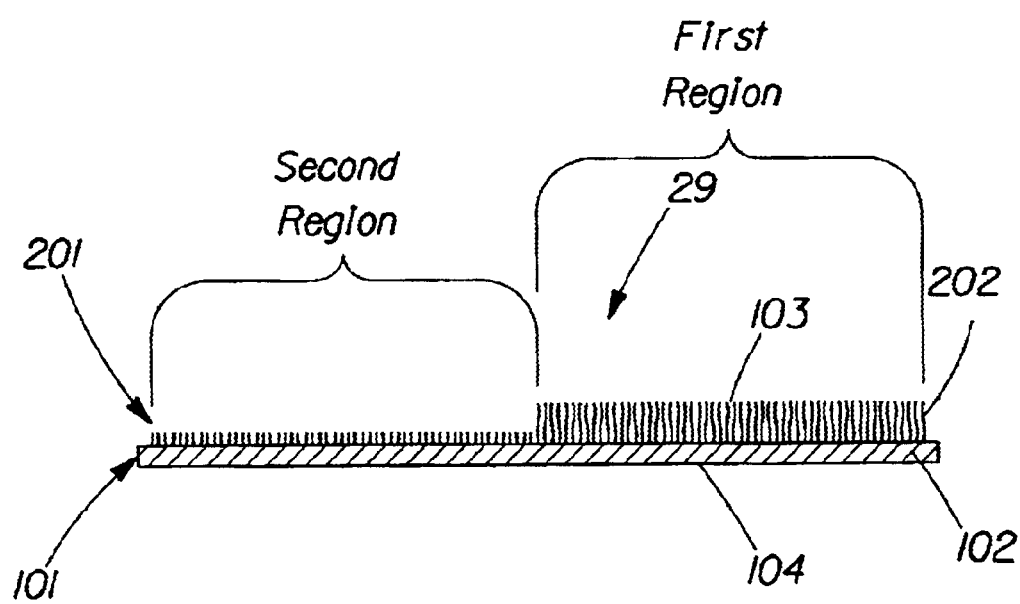
FIG. 3 is a side view of another embodiment of a fecal management member suitable for the present invention.

It is certified that error appears in the above-identified patent and that said Letters Patent is hereby corrected as shown below:

Column 5,
Line 2, after "region", insert -- , see FIG. 3 --.

Column 6,
Line 65, delete "Sep. 10, 1996" and insert -- Oct. 29, 1996 --.

Column 7,
Line 40, delete "No. 081744,487" and insert -- No. 08/744,487 --.

Column 9,
Line 21, delete "wearers" and insert -- wearer's --.
Line 61, delete "WO 95/124173" and insert -- WO 95/24173 --.

Signed and Sealed this

Twenty-first Day of March, 2006

JON W. DUDAS
*Director of the United States Patent and Trademark Office*